(12) United States Patent
Liu et al.

(10) Patent No.: US 9,884,801 B2
(45) Date of Patent: Feb. 6, 2018

(54) **COMPOUNDS FROM *ANTRODIA CAMPHORATA*, METHOD FOR PREPARING THE SAME AND USE THEREOF**

(71) Applicant: ONENESS BIOTECH CO.,LTD., Taipei (TW)

(72) Inventors: Chiung-Lin Liu, Taipei (TW); Wei-Tse Tsai, Taipei (TW); Kai-Hsin Hsieh, Taipei (TW)

(73) Assignee: Oneness Biotech Co., Ltd., Taipei (TW)

( * ) Notice: Subject to any disclaimer, the term of this patent is extended or adjusted under 35 U.S.C. 154(b) by 0 days.

(21) Appl. No.: 14/984,442

(22) Filed: Dec. 30, 2015

(65) Prior Publication Data

US 2016/0185703 A1    Jun. 30, 2016

Related U.S. Application Data

(60) Provisional application No. 62/098,177, filed on Dec. 30, 2014.

(51) Int. Cl.
*A61K 31/122* (2006.01)
*C07C 49/753* (2006.01)

(52) U.S. Cl.
CPC ........ *C07C 49/753* (2013.01); *C07C 2101/16* (2013.01)

(58) Field of Classification Search
CPC .............................. A61K 31/12; A61K 31/122
USPC ......................................................... 514/690
See application file for complete search history.

(56) References Cited

FOREIGN PATENT DOCUMENTS

WO    WO 2012/170720    * 12/2012

* cited by examiner

*Primary Examiner* — Yong Chu
*Assistant Examiner* — Sonya Wright
(74) *Attorney, Agent, or Firm* — Muncy, Geissler, Olds & Lowe, P.C.

(57) ABSTRACT

The invention relates to bioactive compounds purified from mycelium of *Antrodia camphorata* and the manufacturing method thereof. A method for treatment of cancers by administrating an effective amount of the said compounds selected from the group consisting of AC006, AC007, AC009, AC011, AC012, AC007-H1, AC009-H1, and AC012-H1 wherein the cancers is liver cancer, brain cancer, prostate cancer, breast cancer, colorectal cancer, or melanoma.

2 Claims, 1 Drawing Sheet

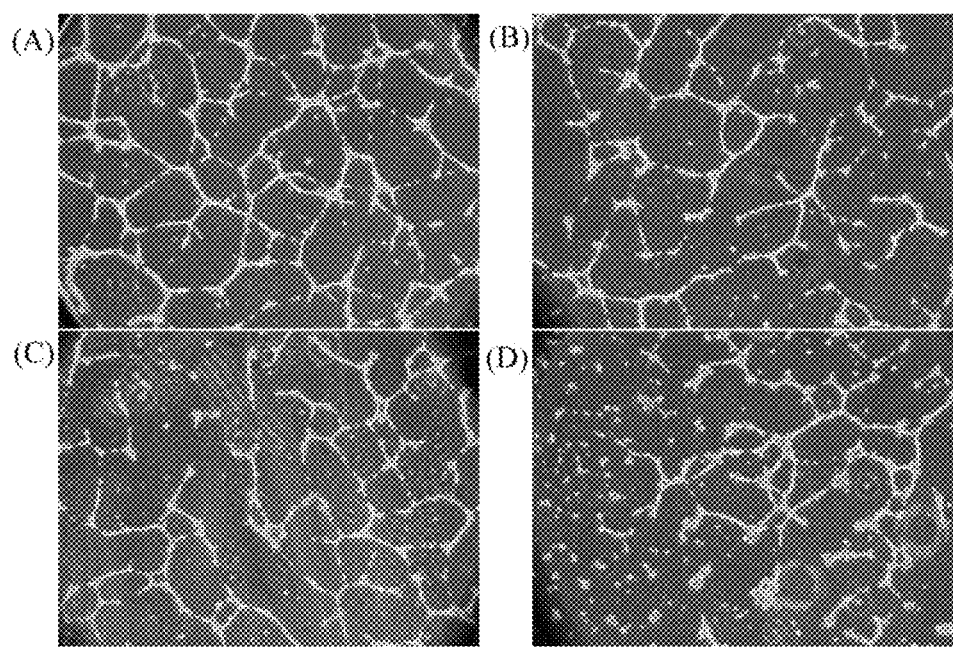

COMPOUNDS FROM *ANTRODIA CAMPHORATA*, METHOD FOR PREPARING THE SAME AND USE THEREOF

CROSS-REFERENCE TO RELATED APPLICATIONS

The present application claims priority to U.S. provisional application No. 62/098,177, filed on Dec. 30, 2014, for which the benefit is claimed under 35 U.S.C. §119; the content of the aforementioned application is hereby incorporated by reference herein in its entirety.

BACKGROUND OF THE INVENTION

1. Field of the Invention

The present invention relates to compounds purified from *Antrodia camphorata*, the methods for preparing the same and the use thereof; particularly the compounds inhibit proliferation of cancer cells and angiogenesis, and are utilized for treatment of cancer.

2. Description of the Prior Art

*Antrodia camphorata* (originally named as *Antrodia cinnamomea*) is a Taiwanese endemic fungus growing in the hollow trunk of *Cinnamomum kanchirai* Hayata, Lauraceae. In folk medicine, *Antrodia camphorata* is a useful antidote for the intoxication of food or pesticide; it is also used for treatment of hepatitis or other liver diseases. Regarding its high medical value, difficulty in culturing, and slow growth rate, several researches in genomics and metabolomics were published for further understanding about the medical use and culturing method of *Antrodia camphorata* (Lu et al. 2014 PNAS、Lin et al. 2011 J Agr Food Chem).

*Antrodia camphorata* comprises an amount of bioactive compound which is capable of medical use, including large molecule polysaccharide and small molecule terpenes. The polysaccharide consist of various monosaccharide units, most of which is 1,3-β-D-glucan, identified by spectrometry. It was reported that polysaccharides of *Antrodia camphorata* have diverse medical use, such as inhibiting angiogenesis (Yang et al. 2009 J Ethnopharmacol、Cheng et al. 2005 Life Sci), inhibiting immune response (Meng et al. 2012 Nutrition), modulating immune response and inhibiting asthma (Liu et al. 2010 Immunology), inhibiting hepatitis B (Lee et al. 2002 FEMS Microbiol Lett), inhibiting cancer cell proliferation (Liu et al. 2004 Toxicol Appl Pharmacol、Lee et al. 2014 Food Funct); also, it was reported that antrodan, a glycoprotein extracted from *Antrodia camphorata*, provides hepatoprotective effect (Ker et al. 2014 PLoS ONE, TW500628, U.S. Pat. No. 7,763,723).

Furthermore, triterpenoids is also a major group of medical compounds from *Antrodia camphorata*. First of all, Cherng et al. reported 3 novel ergostane, a group of triterpenoid compounds: antcins A-C(Cherng et al. 1995 J Nat Prod), and other 4 novel triterpenoids compounds: antcins E-F、methyl antcinate G、methyl antcinate H(Cherng et al. 1996 Phytochemistry); following those reports, tens of triterpenoids compounds was reported to be applicable to therapeutic use, such as inhibition of cancer cell proliferation (Wu et al. 2010 J Nat Prod), inhibition of inflammation (Liaw et al. 2013 J Nat Prod), treatment of liver cancer and hepatitis (Lien et al. 2014 Molecules), anti-fatigue (Huang et al. 2012 Evid Based Complement Altern Med).

U.S. Pat. No. 7,109,232 discloses 5 novel compounds purified from *Antrodia camphorata* and the use, including anti-inflammation and anti-cancer; U.S. Pat. No. 7,732,482 discloses that the said 5 compounds are effective in suppressing fibrosis of organisms. U.S. Pat. No. 7,342,137 discloses a novel group of compounds from *Antrodia camphorata*, inhibiting various cancer cell lines. U.S. Pat. No. 7,745,647 demonstrates the novel diterpenes from fruiting body of *Antrodia camphorata* and their use as a neuroprotective agent. U.S. Pat. No. 7,994,158 provides the dehydrosulphurenic acid purified from *Antrodia camphorata* inhibits the proliferation of cancer, especially leukemia and pancreatic cancer; furthermore, U.S. Pat. No. 7,531,627 provides a 29 kDa novel protein ACA1 from *Antrodia camphorata*, which enhances inflammation and has potential for treatment of cancer.

The mechanisms by which Antrodia compounds inhibit cancer differ according to the chemical structure. Yeh et al. reported that sesquiterpene lactone antrocin suppresses JAK2/STAT3 signaling pathway and induces apoptosis (Yeh et al. 2013 Carcinogenesis); Yang et al. reports that Antrodia extract suppresses HER-2/neu pathway and inhibits ovarian cancer (Yang et al. 2013 J Ethnopharmacol); in addition, Wang et al. reported antroquinonol D cause DNA demethylation and has potential for treating cancer (Wang et al. 2014 J Agric Food Chem).

In sum, *Antrodia camphorata* has an amount of substances having potential for treating cancers, some of which were proved to be effective against various cancers. However, little is known about if there are still other undiscovered novel compounds and its anticancer effect. Present invention extracts a number of compounds from *Antrodia camphorata*, identifies their structures and investigates their effects on various diseases.

SUMMARY OF THE INVENTION

In one aspect, the present invention provides the compound shown as AC007-H1

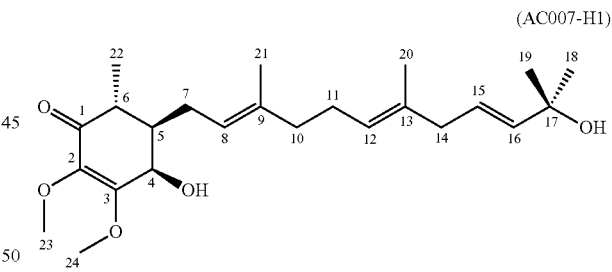

In another aspect, the present invention provides the compound shown as AC009-H1

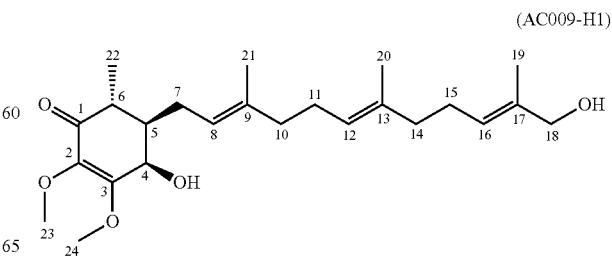

In another aspect, the present invention provides the compound shown as AC012-H1

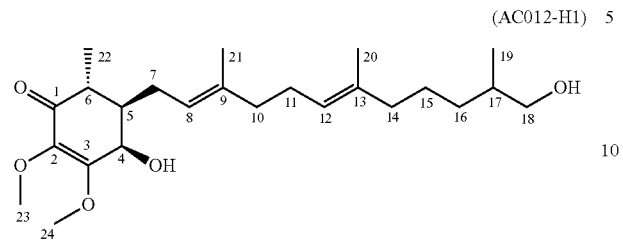

(AC012-H1)

In another aspect, the present invention provides a pharmaceutical composition for treatment of cancer comprising the therapeutically effective amount of compound selecting from the group consisting of AC006, AC007, AC009, AC011, AC012, AC007-H1, AC009-H1 and AC012-H1 or the combination of at least two of the said compounds, and pharmaceutically acceptable vehicles, salts, or prodrugs.

In one embodiment, the vehicles include excipients, diluents, thickeners, fillers, binders, disintegrants, lubricants, oil or non-oil agents, surfactants, suspending agents, gelling agents, adjuvants, preservatives, antioxidants, stabilizers, coloring agents, or spices thereof.

In another embodiment, the treatment of cancer is via inhibition of cancer cell proliferation.

In another embodiment, the pharmaceutical composition is formulated for intravenous injection, subcutaneous injection, oral administration, or topical administration.

In other embodiment, the pharmaceutical composition is a tablet, a pill, a capsule, a liquid, a suspension, a gel, a dispersion, a solution, an emulsion, an ointment, or a lotion.

In another aspect, the present invention provides a method for treatment of cancer by administering an effective dosage of pharmaceutical composition, wherein the pharmaceutical composition comprises the compound according to the aforementioned composition.

In one embodiment, the cancer is selected from the group consisting of prostate cancer, liver cancer, melanoma, brain cancer, and colorectal cancer.

In the preferred embodiment, the cancer is colorectal cancer and liver cancer.

In another embodiment, the pharmaceutical composition is administered via intravenous injection, subcutaneous injection, oral administration, or topical administration.

In a further aspect, the present invention provides a method of preparing bioactive compounds and its derivatives from mycelium of *Antrodia camphorata*, comprising the steps of:
extracting mycelium media of *Antrodia camphorata* twice with reflux using hexane for 1-3 hours each time;
combining two hexane extracts after vacuum filtration;
preparing the column with silica gel (70-230 mesh) and mycelia;
eluting with n-hexane/ethyl acetate gradient solutions to obtain fraction F1, F2 and F3, wherein the gradient was 17-22% ethyl acetate, 23-27% ethyl acetate and 28-33% ethyl acetate, respectively, wherein F3 is divided into F3-1, F3-2, F3-3 by retention time;
separating fraction F3-1 by silica gel column chromatography (from 50:1 to 20:1 gradient elution) using $CH_2Cl_2$/Acetone as the mobile phase and collecting the fraction of $CH_2Cl_2$/Acetone=40:1-15:1 for further purification with a normal phase semi-preparative HPLC column and use n-Hexane/Ethyl acetate (4:1) to obtain purified AC006;
separating fraction F3-2 with a normal phase MPLC silica gel column, using $CH_2Cl_2$/Acetone gradient solutions (100%:0% to 70%:30%) as the mobile phase and collecting the fraction of 95%:5% to 85%:15% and divide into three fractions F3-2-1 to F3-2-3;
purifying fraction F3-2-3 by silica gel column chromatography using n-hexane/Ethyl acetate (100%:0% to 0%:100%) as the mobile phase, collecting the fraction of n-hexane/Acetone=90/10-70-30, and further purifying with silica gel column chromatography using n-hexane/Ethyl acetate (100%:0% to 0%:100%) as the mobile phase, obtaining AC007 with the elution solution of n-hexane/Ethyl acetate=60/40;
separating fraction F-3-3 with a normal phase MPLC silica gel column using $CH_2Cl_2$/Acetone (100%:0% to 0%:100%) gradient elution, collecting fractions from 90%:10% to 70%:30% which was then be divided into 5 fractions F3-3-1 to F3-3-5, and further purifying F3-3-5 (the fraction of $CH_2Cl_2$/Acetone=73/27) with a silica gel column using n-hexane/Acetone (95%:5% to 50%:50%) as the mobile phase;
collecting the fractions from 85%:15% to 70%:30% of F3-3-5 and divide into 5 fractions F3-3-5-1 to F3-3-5-5;
separating fraction F3-3-5-1 (n-hexane/Acetone=90/10-80/20) by reverse phase MPLC C-18 column purification using 1% formic acid in $H_2O$/methanol=35/65~20/80 gradient as the mobile phase, collecting the fraction of 1% formic acid in $H_2O$/Methanol=28/72-22/78 for purification by silica gel column chromatography with n-hexane/Ethyl acetate as the mobile phase and gradient elution (80%:20% to 50%:50%), and obtaining AC012 with the elution solution of n-hexane/Ethyl acetate (75%:25%-65%:35%).
separating F3-3-5-3 by reverse phase MPLC C-18 silica gel column chromatography using 1% formic acid in $H_2O$/Methanol=25/75 and isocratic elution with 15 ml per minute as the mobile phase, and further purifying the fraction at 130-170 minutes of retention time with silica gel gradient solutions (100%:0% to 0%:100%) by using $CH_2Cl_2$/Ethyl acetate as the mobile phase to collect AC009 with the elution solution of $CH_2Cl_2$/Ethyl acetate=80/20-60/40;
separating fraction F3-3-5-4 (n-hexane/Acetone=76/24) and purify by reverse phase HPLC C-18 column chromatography using 1% formic acid in $H_2O$/Methanol=25%:75% and isocratic elution as the mobile phase to obtain AC011;
wherein the compounds AC006, AC007, AC009, AC011 and AC012 are the bioactive compounds of *Antrodia camphorata*.

In the preferred embodiment, the said compound is further manufactured to obtain bioactive derivatives of hydroxyl group substitution on C4 of the compounds by the steps comprising:
hydrolyzing the compound in 1 equivalent mole of methanol;
after previous reaction is completed, adding acidic amberlite and then filtering by filter membrane to obtain the intermediate product;
eluting the intermediate product by silica gel chromatography, using silica gel as separating resin, gradient of hexane and ethyl acetate as mobile phase, wherein the eluting gradient of hexane:ethyl acetate is from 4:1 to 1:1;

the product is eluted out at approximately 1:1 ratio of the gradient solution;

purifying the product by reverse phase HPLC, using C18 semi-preparative column and solution of methanol: 0.1% FA buffer (phosphate buffered saline)=75:25 as isocratic eluant to obtain bioactive derivatives of hydroxyl group substitution on C4.

In addition, present invention also provides an anti-angiogenic and anti-proliferative composition comprising of the abovementioned substances of *Antrodia camphorata*, proper diluent, excipient, or vehicle; moreover, the composition can inhibit proliferation of highly proliferative cells.

BRIEF DESCRIPTION OF THE DRAWINGS

The present invention will become more fully understood from the detailed description given herein below and the accompanying drawings which are given by way of illustration only, and thus are not limitative of the present invention, and wherein:

The FIGURE shows the anti-angiogenic effect of the extract AC012 in vitro and (A) control group, (B) AC012 0.1 µg/ml, (C) AC012 0.3 µg/ml and (D) AC012 1 µg/ml was separately added to EPC cell culture.

DETAILED DESCRIPTION OF THE PREFERRED EMBODIMENT

Unless defined otherwise, all technical and scientific terms used herein have the meaning commonly understood by a person skilled in the art to which this invention belongs. As used herein, the following terms have the meanings ascribed to them unless specified otherwise. The present invention will now be described more specifically with reference to the following embodiments, which are provided for the purpose of demonstration rather than limitation; however, it should be understood that the present invention is not limited to the preferred embodiments shown. Unless otherwise specified, all materials used herein are commercially available materials and can be easily acquired.

The term "treatment", "under treatment" and similar terms refer to the methods which ameliorate, improve, reduce or reverse the patient's disease or any relevant symptoms caused by the disease, or methods which can prevent onset of such diseases or any resulting symptoms.

The term "pharmaceutically acceptable" is used to describe substances to be used in the composition must be compatible with other ingredients in the formulation and be harmless to the subject.

The inventive composition can be prepared into a dosage form for suitable application of the inventive composition by using technology commonly understood by a person skilled in the art through formulating the abovementioned compound(s) with a pharmaceutically acceptable vehicle, wherein the excipients include, but are not limited to, solution, emulsion, suspension, powder, tablet, pill, lozenge, troche, chewing gum, slurry, and other suitable forms.

The "pharmaceutically acceptable vehicle" may contain one or several reagents selecting form the following list: solvents, emulsifiers, suspending agents, decomposers, binding agents, excipients, stabilizing agents, chelating agents, diluents, gelling agents, preservatives, lubricants, surfactants and other agents suitable for use in the invention.

In the abovementioned compositions, one or more dissolving aids, buffers, preservatives, colorants, fragrances, flavoring agents and the like, which are commonly used for formulation can be added as desired.

The term "pharmaceutically acceptable excipients", as used herein, refers to substances known by persons skilled in the art, which are physiologically inert, pharmacologically inactive and are compatible with the physical as well as chemical characteristics of provided compound(s). Pharmaceutically acceptable excipients include, but are not limited to, polymers, plasticizers, fillers, lubricants, diluents, binders, disintegrants, solvents, co-solvents, surfactants, preservatives, sweetening agents, flavoring agents, pharmaceutical grade dyes or pigments, and viscosity agents.

The term "pharmaceutical composition" is used to describe solid or liquid compositions in a form, concentration and purity that are suitable for administration in patients and can induce desired physiological changes following administration. Pharmaceutical compositions are typically sterile and non-pyrogenic.

The term "effective dosage" as used herein refers to the necessary dosage to cause, elicit, or contribute to the expected biological response. As is known by a skilled person in the art, the effective dosage of a pharmaceutical composition varies depending on the following factors, including desired biological endpoint, the drug to be delivered, the composition of the encapsulating matrix, the target tissue, etc.

Example 1: Preparation of the Active Substances from *Antrodia camphorata*

The mycelium media of *Antrodia camphorata* was extracted twice with reflux using hexane for 1-3 hrs each time and the two hexane extracts were combined after vacuum filtration. A column was prepared using silica gel (70-230 mesh) and mycelia and eluted with n-hexane/Ethyl acetate gradient solutions to obtain fraction F1, F2 and F3 and the corresponding gradient elution was 17-22% Ethyl acetate, 23-27% Ethyl acetate and 28-33% Ethyl acetate, respectively. The resulting fraction F3 was divided into F3-1~F3-3 three fractions by retention time.

Separate fraction F3-1 by silica gel column chromatography (from 50:1 to 20:1 gradient elution) using $CH_2Cl_2$/Acetone as the mobile phase and collect the fraction of 40:1-15:1 for further purification with a normal phase semi-preparative HPLC column and use n-Hexane/Ethyl acetate (4:1) to obtain purified AC006.

Separate fraction F3-2 with a normal phase MPLC silica gel column and use $CH_2Cl_2$/Acetone gradient solutions (100%:0% to 70%:30%) as the mobile phase. Collect the fraction of 95%:5% to 85%:15% and divide into three fractions and further purify fraction F3-2-3 by silica gel column chromatography using n-hexane/Ethyl acetate (100%:0% to 0%:100%) as the mobile phase and collect the fraction of n-hexane/Acetone=90/10-70-30. Continue on purification by silica gel column chromatography using n-hexane/Ethyl acetate (100%:0% to 0%:100%) as the mobile phase and obtain AC007 with the elution solution of n-hexane/Ethyl acetate=60/40.

Separate fraction F-3-3 with a normal phase MPLC silica gel column using $CH_2Cl_2$/Acetone (100%:0% to 0%:100%) gradient elution and collect fractions from 90%:10% to 70%:30% which was then be divided into 5 fractions. Further purify F-3-3-5 (the fraction of $CH_2Cl_2$/Acetone=73/27) with a silica gel column using n-hexane/Acetone (95%:5% to 50%:50%) as the mobile phase. Collect the fractions from 85%:15% to 70%:30% and divide into 5 fractions. Take F3-3-5-1 (n-hexane/Acetone=90/10-80/20) for reverse phase MPLC C-18 column purification using 1% formic acid in $H_2O$/methanol=35/65~20/80 gradient as the mobile phase. Take the fraction of 1% formic acid in H₂O/Methanol=28/72-22/78 for purification by silica gel column chromatography with n-hexane/Ethyl acetate as the mobile phase and gradient elution (80%:20% to 50%:50%) and obtain AC012 with the elution solution of n-hexane/Ethyl acetate (75%:25%-65%:35%).

Separate F3-3-5-3 by reverse phase MPLC C-18 silica gel column chromatography and use 1% formic acid in H₂O/Methanol=25/75 and isocratic elution with 15 ml per minute as the mobile phase to obtain the fraction containing most of AC009, and then further purify the fraction at 130-170 minutes of retention time with silica gel gradient solutions (100%:0% to 0%:100%) by using CH₂Cl₂/Ethyl acetate as the mobile phase and collect AC009 with the elution solution of CH₂Cl₂/Ethyl acetate=80/20-60/40.

Take F3-1 and purify by reverse phase HPLC C-18 column chromatography using a mobile phase of 1% formic acid/methanol=25%:75% isocratic to obtain AC-05-01.

Take fraction F3-3-5-4 (n-hexane/Acetone=76/24) and purify by reverse phase HPLC C-18 column chromatography using 1% formic acid in H₂O/Methanol=25%:75% and isocratic elution as the mobile phase to obtain AC011.

Wherein, the extracts AC006, AC007, AC009, AC011 and AC012 are the bioactive compounds of *Antrodia camphorata*.

Example 2 Chemical Structure of Active Substances Purified from Mycelia of *Antrodia camphorata*

The compounds were identified by spectroscopic methods, including 1D and 2D nuclear magnetic resonance (NMR) and mass spectral analyses. The structure is shown in below.

Example 2.1

AC006

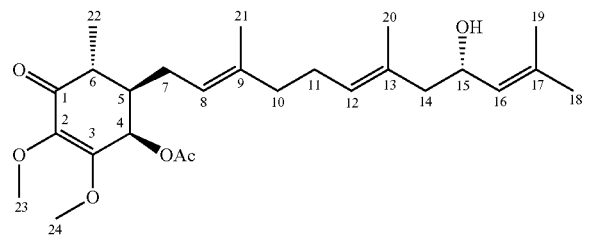

EIMS, m/z 471.2701 [M+Na]+; $^1$H NMR (400 MHz, CD₃OD) δ 5.77 (1H, d, J=3.2 Hz, H-4), 5.18 (1H, t, J=5.6 Hz, H-12), 5.16 (1H, t, J=6.4 Hz, H-8), 5.11 (1H, dt, J=1.6, 8.8 Hz, H-16), 4.43 (1H, q, J=6.8, H-15), 4.00 (3H, s, H-24), 3.62 (3H, s, H-23), 2.53 (1H, m, H-6), 2.29 (1H, m, H-7a), 2.24 (2H, m, H-14), 2.11 (2H, m, H-11), 2.10 (3H, s, —OAc), 2.08 (1H, m, H-10a), 2.02 (1H, m, H-7b), 1.94 (1H, m, H-10b), 1.92 (1H, m, H-5), 1.71 (3H, d, J=1.2 Hz, H-18), 1.66 (3H, d, J=1.2 Hz, H-19), 1.64 (3H, s, H-20), 1.58 (3H, s, H-21), 1.18 (3H, d, J=6.8 Hz, H-22); $^{13}$C NMR (100 MHz, CD₃OD) δ 199.2 (s, C-1), 171.6 (s, —COCH₃), 160.7 (s, C-3), 138.9 (s, C-2), 138.8 (s, C-9), 134.9 (s, C-17), 132.9 (s, C-13), 129.6 (d, C-16), 128.4 (d, C-12), 122.2 (d, C-8), 70.4 (d, C-4), 68.1 (d, C-15), 61.2 (q, C-23), 60.4 (q, C-24), 49.2 (t, C-14), 44.4 (d, C-5), 42.6 (d, C-6), 40.9 (t, C-10), 28.1 (t, C-7), 27.6 (t, C-11), 26.1 (q, C-18), 21.0 (q, —COCH₃), 18.5 (q, C-19), 16.8 (q, C-20), 16.5 (q, C-21), 13.3 (q, C-22).

Example 2.2

AC007

EIMS, m/z 471.2690 [M+Na]+; 1H NMR (400 MHz, CD3OD) δ 5.76 (1H, d, J=3.1 Hz, H-4), 5.57 (1H, m, H-16), 5.55 (1H, m, H-15), 5.16 (1H, t, J=7.3 Hz, H-12), 5.15 (1H, t, J=7.1 Hz, H-8), 3.99 (3H, s, H-24), 3.61 (3H, s, H-23), 2.52 (1H, m, H-6), 2.27 (1H, m, H-7a), 2.11

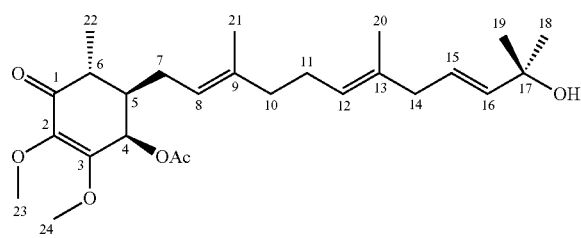

(2H, m, H-11), 2.10 (3H, s, —OAc), 2.02 (1H, m, H-7b), 2.00 (2H, m, H-10), 1.93 (1H, m, H-5), 1.59 (3H, s, H-20), 1.58 (2H, d, J=8.0 Hz, H-14), 1.57 (3H, s, H-21), 1.25 (3H, s, H-19), 1.25 (3H, s, H-18), 1.17 (3H, d, J=7.0 Hz, H-22); 13C NMR (100 MHz, CD3OD) δ 199.1 (s, C-1), 171.4 (s, —COCH3), 160.6 (s, C-3), 140.5 (d, C-16), 138.9 (s, C-2), 138.7 (s, C-9), 135.1 (s, C-13), 126.2 (d, C-15), 126.1 (d, C-12), 122.1 (d, C-8), 71.1 (s, C-17), 70.3 (d, C-4), 61.1 (q, C-23), 60.2 (q, C-24), 44.2 (d, C-5), 43.5 (t, C-14), 42.5 (d, C-6), 40.8 (t, C-10), 30.0 (q, C-18), 30.0 (q, C-19), 28.0 (t, C-7), 27.5 (t, C-11), 20.8 (q, —COCH3), 16.3 (q, C-21), 16.1 (q, C-20), 13.1 (q, C-22).

Example 2.3

AC009

EIMS, m/z 471.26498 [M+Na]+; 1H NMR (400 MHz, CD3OD) δ 5.77 (1H, d, J=3.2 Hz, H-4), 5.39 (1H, td, J=7.2, 1.2 Hz, H-16), 5.16 (1H, td, J=7.2, 0.8 Hz, H-12), 5.16 (1H, td, J=7.2, 0.8 Hz, H-8), 4.00 (3H, s, H-23), 3.91 (2H, s, H-18), 3.62 (3H, s, H-24), 2.53 (1H, m, H-6),

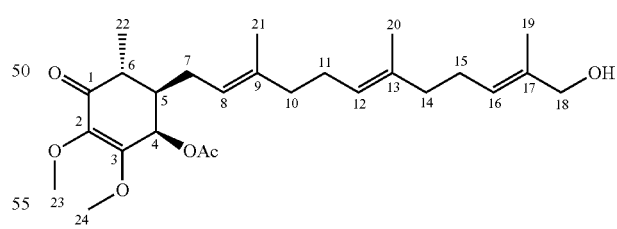

2.28 (1H, m, H-7a), 2.14 (2H, m, H-11), 2.14 (2H, m, H-15), 2.10 (3H, s, —OAc), 2.04 (1H, m, H-7b), 2.03 (2H, m, H-10), 2.03 (2H, m, H-14), 1.92 (1H, m, H-5), 1.64 (3H, s, H-19), 1.62 (3H, s, H-20), 1.58 (3H, s, H-21), 1.18 (3H, d, J=7.2 Hz, H-22); 13C NMR (100 MHz, CD3OD) δ 199.2 (s, C-1), 171.6 (s, —COCH3), 160.8 (s, C-3), 138.9 (s, C-2), 138.8 (s, C-9), 136.0 (s, C-13), 136.0 (s, C-17), 126.7 (d, C-16), 125.7 (d, C-12), 122.2 (d, C-8), 70.5 (d, C-4), 69.1 (t, C-18), 61.3 (q, C-24), 60.4 (q, C-23), 44.4 (d, C-5), 42.6 (d, C-6), 41.0 (t, C-10), 40.7 (t, C-14), 28.1 (t, C-7), 27.6 (t,

C-16), 27.5 (t, C-11), 21.0 (q, —COCH3), 16.5 (q, C-21), 16.3 (q, C-20), 13.9 (q, C-19), 13.1 (q, C-22).

Example 2.4

AC012

EIMS, m/z 473.2846 [M+Na]+; 1H NMR (400 MHz, CD3OD) δ 5.77 (1H, d, J=3.2 Hz, H-4), 5.16 (1H, t, J=7.6 Hz, H-8), 5.13 (1H, t, J=7.2 Hz, H-12), 4.00 (3H, s, H-24), 3.62 (3H, s, H-23), 3.38 (1H, d, J=10.2 Hz, H-18a), 3.31 (1H, d, J=5.6 Hz, H-18b), 2.53 (1H, m,

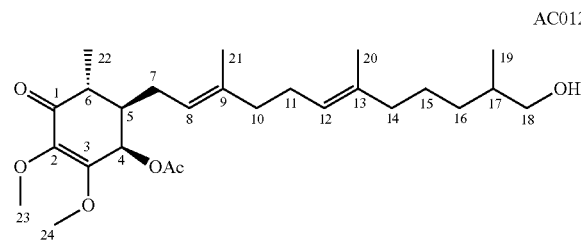

AC012

H-6), 2.26 (1H, m, H-7a), 2.13 (2H, m, H-11), 2.10 (3H, s, —OAc), 2.04 (1H, m, H-7b), 2.00 (2H, m, H-10), 1.96 (2H, m, H-14), 1.93 (1H, m, H-5), 1.60 (3H, s, H-20), 1.58 (3H, s, H-21), 1.56 (1H, m, H-17), 1.36 (2H, m, H-15), 1.06 (2H, m, H-16), 1.06 (3H, d, J=4.8 Hz, H-22), 0.90 (3H, d, J=6.8 Hz, H-19); 13C NMR (100 MHz, CD3OD) δ 198.9 (s, C-1), 171.3 (s, —COCH3), 160.5 (s, C-3), 138.7 (s, C-9), 138.6 (s, C-2), 136.2 (s, C-13), 125.3 (d, C-12), 122.0 (d, C-8), 70.3 (d, C-4), 68.4 (t, C-18), 61.1 (q, C-23), 60.2 (q, C-24), 44.2 (d, C-5), 42.5 (d, C-6), 41.0 (t, C-14), 40.9 (t, C-10), 36.8 (d, C-17), 34.0 (t, C-16), 28.0 (t, C-7), 27.4 (t, C-11), 26.5 (t, C-15), 20.9 (q, —COCH3), 17.2 (q, C-19), 16.4 (q, C-21), 16.0 (q, C-20), 13.2 (q, C-22).

Example 2.5

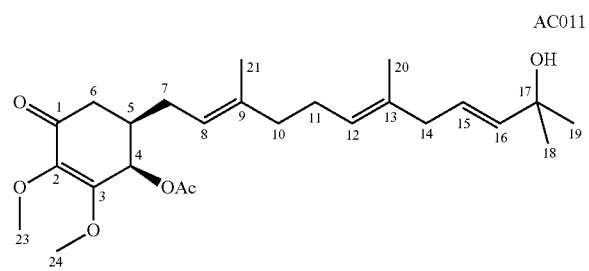

AC011

EIMS, m/z 475.2553 [M+Na]+; 1H NMR (400 MHz, CD3OD) δ 5.81 (1H, d, J=3.2 Hz, H-4), 5.57 (1H, m, H-16), 5.55 (1H, m, H-15), 5.15 (1H, t, J=6.8 Hz, H-12), 5.12 (1H, t, J=7.2 Hz, H-8), 3.99 (3H, s, H-23), 3.62 (3H, s, H-22), 2.66 (1H, d, J=5.2 Hz, H-14), 2.38 (2H, m, H-6), 2.09 (3H, s, —OAc), 2.05 (2H, m, H-11), 2.03 (1H, m, H-7a), 2.01 (2H, m, H-10), 1.99 (1H, m, H-7b), 1.92 (1H, m, H-5), 1.58 (3H, s, H-20), 1.58 (3H, s, H-21), 1.25 (3H, s, H-19), 1.25 (3H, s, H-18); 13C NMR (100 MHz, CD3OD) 197.1 (s, C-1), 171.6 (s, —COCH3), 161.8 (s, C-3), 140.5 (d, C-15), 139.5 (s, C-2), 135.2 (s, C-13), 126.2 (d, C-16), 126.0 (d, C-12), 122.2 (d, C-8), 121.9 (s, C-9), 71.1 (s, C-17), 71.1 (d, C-4), 61.1 (q, C-22), 60.0 (q, C-23), 43.5 (t, C-14), 40.8 (t, C-10), 39.2 (t, C-6), 38.3 (d, C-5), 30.1 (t, C-7), 30.0 (q, C-18), 30.0 (q, C-19), 27.5 (t, C-11), 20.7 (q, —COCH3), 16.3 (q, C-21), 16.2 (q, C-20).

Example 2.6

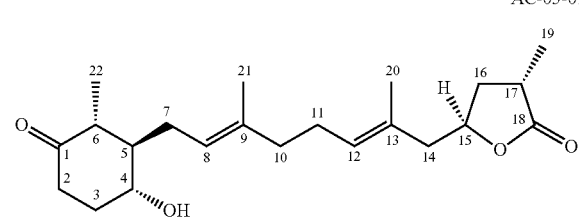

AC-05-01

EIMS, m/z 385.2379 [M+Na]+; 1H NMR (400 MHz, CD3OD) δ 5.25 (1H, t, J=4.3 Hz, H-12), 5.20 (1H, t, J=4.8 Hz, H-8), 4.69 (1H, m, H-15), 4.16 (1H, q, J=4.1 Hz, H-4), 2.73 (1H, m, H-17), 2.36 (1H, m, H-14a), 2.31 (1H, m, H-6), 2.29 (1H, m, H-7a), 2.27 (2H, m, H-3), 2.23 (1H, m, H-14b), 2.19 (1H, m, H-16a), 2.16 (2H, m, H-11), 2.08 (2H, m, H-10), 2.02 (1H, m, H-7b), 1.98 (1H, m, H-16b), 1.88 (2H, m, H-2), 1.67 (3H, s, H-20), 1.65 (3H, s, H-21), 1.41 (1H, m, H-5), 1.23 (3H, d, J=4.9 Hz, H-19), 1.06 (3H, d, J=4.3 Hz, H-22); 13C NMR (100 MHz, CD3OD) δ 213.8 (s, C-1), 182.7 (s, H-18), 137.9 (s, C-9), 131.8 (s, C-13), 129.3 (d, C-12), 122.7 (d, C-8), 78.8 (d, C-15), 76.2 (d, C-4), 48.6 (d, C-6), 48.2 (d, C-5), 46.0 (t, C-14), 40.6 (t, C-10), 36.6 (t, C-3), 35.7 (t, C-16), 35.1 (d, C-17), 32.9 (t, C-7), 29.6 (t, C-2), 27.5 (t, C-11), 16.5 (q, C-20), 16.3 (q, C-21), 16.0 (q, C-19), 11.8 (q, C-22).

Example 3 Modification of Substituent of Compounds Purified from Mycelia of *Antrodia camphorata*

After identification of the chemical structure, the purified compounds were subsequently modified to substitute the substituent of C4 and C3. The method of modification is described in the following. The new compounds with hydroxyl group (—OH) on C4 are marked "H1"; the new compounds with hydroxyl group on C4 and additionally dimethoxy group on C3 are marked "H2"

AC012 was hydrolyzed in 1 N (equivalent mole) of NaOMe (sodium methoxide) and anhydrous methanol, respectively. During the hydrolyzation, the reaction was monitored by TLC (thin layer chromatography) until the reaction had been completed. After completion, acidic amberlite was added to neutralize and then was filtered by filter membrane to obtain the intermediate product.

The intermediate product was eluted by normal phase silica gel chromatography, using silica gel as separating resin, gradient of hexane and ethyl acetate as mobile phase, wherein the eluting gradient of hexane:ethyl acetate is from 4:1 to 1:1. As the process of elution was monitored by TLC, the mixture of products (AC012-H1 and AC012-H2) was eluted out at approximately 1:1 ratio of the gradient solution, and then was collected and condensed.

The purification of respective product was performed by reverse phase HPLC, using C18 semi-preparative column and solution of methanol: 0.1% FA buffer (phosphate buffered saline)=75:25 as isocratic eluant. The retention time to collect AC012-H1 was from 31 to 25 minutes; the retention time to collect AC012-H2 was from 39 to 43 minutes.

The chemical structure of AC012-H1 and AC012-H2 are shown in the following:

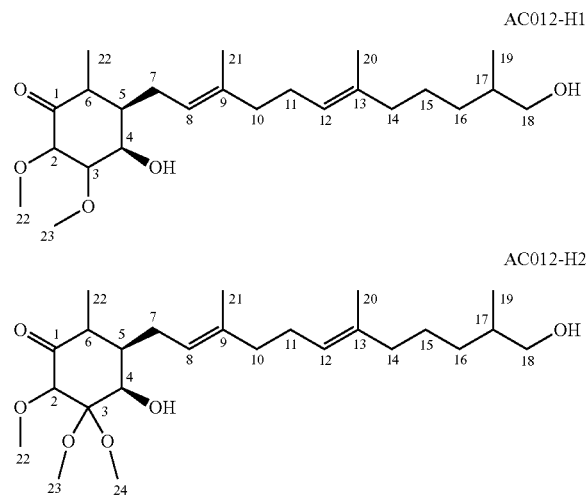

AC012-H1

AC012-H2

The same modifying method in this example can be applied to other purified compounds in the present invention to render the similar substitution.

If the initial input reactant was AC007, the retention time to collect AC007-H1 was from 36 to 43 minutes; AC007-H2, from 47 to 53 minutes.

If the initial input reactant was AC009, the retention time to collect AC009-H1 was from 27 to 32 minutes; AC009-H2, from 35 to 40 minutes.

Example 4 Analysis of Anti-Angiogenic Activity of the Active Substances from Mycelia of *Antrodia camphorata*

SRB assay and matrigel capillary tube formation assay were performed to evaluate the anti-angiogenic effect of the purified compounds.

SRB Assay

Endothelial progenitor cell (EPCs, $5\times10^3$ cells/well) were sub-cultured onto 96-well plates and starved with serum-free medium for 48 h. Then cells were incubated in medium with 10% FBS in the absence or presence of various concentrations of AC012 (0.1, 0.3, 1, 3, 10 and 30 μg/ml) for 48 h. After treatment, the medium was discarded firstly. In order to fix the adherent cells, 100 μl of trichloroacetic acid (10% (w/v)) were adding to each well and incubating at 4° C. for 1 hour. Then the plates were then washed with deionized water and dried in the air. Each well were added with 50 μl of Sulforhodamine B (SRB) solution (0.4% w/v in 1% acetic acid) and incubated for 5 min at room temperature. To remove unbound SRB in the plates, the plates were washed with 1% acetic acid and then air dried. The residual bound SRB was solubilized with 100 μl of 10 mM Tris base buffer (pH 10.5), and then read using a micro titer plate reader at 495 nm.

Matrigel Capillary Tube Formation

Matrigel was added to 15-well-plates (ibidi) in a total volume of 10 μl in each well. Plates were stood at 37° C. for 30 min to form a gel layer. After gel formation, EPCs ($5\times10^3$ cells) treated with or without AC012 (0.1, 0.3, 1 μg/ml) in presence of VEGF (20 ng/ml) were applied to each well, and plates were incubated for at 37° C. 16 hr with 5% $CO_2$. After incubation, the inverted contrast phase microscope (Nikon, Japan) was used for subject observation.

The inhibitory concentrations of 50% EPC cell proliferation ($IC_{50}$) was 29 μg/ml. In 1 μg/ml concentration, AC012 was able to inhibit 31.89% tube formation.

Example 5 Analysis of Anti-Proliferation of the Active Substances from Mycelia of *Antrodia camphorata*

The anti-angiogenic effect of the purified compounds implicates anti-proliferative effect on cancer cell; SRB assay was performed to further investigate the anti-proliferative effect of purified compound in various cell lines.

The purpose of the in vitro experiment is to evaluate the effect of AC006, AC007, AC009, AC011 and AC012 on cell proliferation in various cell lines.

Various cell lines ($5\times10^3$ cells/well) were sub-cultured onto 96-well plates and starved with serum-free medium for 48 h. Then cells were incubated in medium with 10% FBS in the absence or presence of various concentrations of AC006, AC007, AC009, and AC012 (0.1, 0.3, 1, 3, 10, and 30 μg/ml) for 48 hours. After treatment, the medium was discarded firstly. After treatment, the medium was discarded firstly. In order to fix the adherent cells, 100 μl of trichloroacetic acid (10% (w/v)) were adding to each well and incubating at 4° C. for 1 hour. Then the plates were then washed with deionized water and dried in the air. Each well were added with 50 μl of Sulforhodamine B (SRB) solution (0.4% w/v in 1% acetic acid) and incubated for 5 min at room temperature. To remove unbound SRB in the plates, the plates were washed with 1% acetic acid and then air dried. The residual bound SRB was solubilized with 100 μl of 10 mM Tris base buffer (pH 10.5), and then read using a micro titer plate reader at 495 nm.

Example 5.1 Results of AC006

Seven cancer cell lines (four types of cancers) are used in this experiment and the inhibitive concentrations of 50% cell proliferation ($IC_{50}$) are listed below:

TABLE 1

| Cell Type | Cell lines | $IC_{50}$ (μg/mL) |
|---|---|---|
| Prostate | PC3 | 19.68 |
| Liver | Huh-7 | 0.72 |
|  | Sk-Hep-1 | 26.76 |
| Melanoma | B16F10 | 28.69 |
| Lung | A549 | >10 (inhibition = 12.21% in 10 μg/ml) |
| Brain | U251 | >30 (inhibition = 22.64% in 30 μg/ml) |
| (Glioma) | U87 | >30 (inhibition = 11.26% in 30 μg/ml) |
|  | LN-229 | >30 (inhibition = 22.58% in 30 μg/ml) |

Example 5.2 Results of AC007

Seven cancer cell lines (five types of cancers) are used in this experiment and the inhibitory concentrations of 50% cell proliferation ($IC_{50}$) are listed below:

TABLE 2

| Cell Type | Cell lines | $IC_{50}$ (μg/mL) |
|---|---|---|
| Melanoma | B16F10 | 23.45 |
| Prostate | PC-3 | 22.06 |
| Breast | 4T-1 | 24.83 |
| Colorectal | DLD-1 | 19.74 |
|  | RKO | 17.60 |
| Brain | LN-229 | >25 (inhibition = 19.1% in 25 μg/ml) |

TABLE 3

| Cell Type | Cell lines | IC$_{50}$ (μg/mL) | | |
|---|---|---|---|---|
| | | AC007 | AC007-H1 | AC007-H2 |
| Lung | A549 | 3.57 | 1.69 | NA |
| Liver | Huh-7 | 0.88 | <0.3 (inhibition = 85.16% in 0.3 μg/ml) | NA |
| Colon rectal | RKO | >10 (inhibition = 29.51% in 10 μg/ml) | >10 (inhibition = 33.03% in 10 μg/ml) | >10 (inhibition = 29.88% in 10 μg/ml) |
| | DLD-1 | >10 (inhibition = 25.58% in 10 μg/ml) | >10 (inhibition = 16.07% in 10 μg/ml) | >10 (inhibition = 27.05% in 10 μg/ml) |
| | SW-480 | >10 (inhibition = 21.47% in 10 μg/ml) | >10 (inhibition = 18.19% in 10 μg/ml) | >10 (inhibition = 25.74% in 10 μg/ml) |
| | HCT-116 | 0.93 | <0.3 (inhibition = 59.50% in 0.3 μg/ml) | >10 (inhibition = 48.03% in 10 μg/ml) |

Example 5.3 Results of AC009

Ten cancer cell lines (four types of cancers) are used in this experiment and the inhibitory concentrations of 50% cell proliferation (IC$_{50}$) are listed below:

TABLE 4

| Cell Type | Cell lines | IC$_{50}$ (μg/mL) |
|---|---|---|
| Prostate | PC3 | 14.99 |
| Melanoma | B16F10 | 22.43 |
| Colon | RKO | 15.94 |
| | NST | >25 (inhibition = 44.42% in 25 μg/ml) |
| | HT-29 | 33.23 |
| | SW480 | 18.55 |
| | DLD-1 | 14.61 |
| | COLO205 | 2.45 |
| Brain | LN-229 | 19.5 |

TABLE 5

| Cell Type | Cell lines | IC$_{50}$ (μg/mL) | | |
|---|---|---|---|---|
| | | AC009 | AC009-H1 | AC009-H2 |
| Lung | A549 | 8.08 | >10 (inhibition = 40.79% in 10 μg/ml) | NA |
| Liver | Huh-7 | <0.3 (inhibition = 88.17% in 0.3 μg/ml) | <0.3 (inhibition = 90.59% in 0.3 μg/ml) | NA |
| Colon rectal | RKO | >10 (inhibition = 33.22% in 10 μg/ml) | >10 (inhibition = 8.79% in 10 μg/ml) | >10 (inhibition = 47.01% in 10 μg/ml) |
| | DLD-1 | >10 (inhibition = 8.75% in 10 μg/ml) | >10 (inhibition = 11.04% in 10 μg/ml) | >10 (inhibition = 9.46% in 10 μg/ml) |
| | SW-480 | >10 (inhibition = 7.98% in 10 μg/ml) | >10 (inhibition = 4.01% in 10 μg/ml) | >10 (inhibition = 14.94% in 10 μg/ml) |
| | HCT-116 | 2.56 | <0.3 (inhibition = 54.42% in 0.3 μg/ml) | >10 (inhibition = 48.94% in 10 μg/ml) |

Example 5.4 Results of AC011

Four cancer cell lines are used in this experiment and the inhibitory concentrations of 50% cell proliferation (IC$_{50}$) are listed below:

TABLE 6

| Cell Type | Cell lines | IC$_{50}$ (μg/mL) |
|---|---|---|
| Colon rectal | RKO | >10 (inhibition = 24.13% in 10 μg/ml) |
| | DLD-1 | >10 (inhibition = 7.57% in 10 μg/ml) |
| | SW-480 | >10 (inhibition = 31.56% in 10 μg/ml) |
| | HCT-116 | 2.43 |

Example 5.4 Results of AC012

Eight cancer cell lines (five types of cancers) are used in this experiment and the inhibitory concentrations of 50% cell proliferation (IC$_{50}$) are listed below:

TABLE 7

| Cell Type | Cell lines | IC$_{50}$ (μg/mL) |
|---|---|---|
| Prostate | PC3 | 11.36 |
| Liver | Sk-Hep-1 | 8.27 |
| Melanoma | B16F10 | 9.16 |
| Brain | U251 | 22.72 |
| (Glioma) | U87 | 18.63 |
| | LN-229 | 19.45 |

TABLE 8

| Cell Type | Cell lines | IC$_{50}$ (μg/mL) AC012 | AC012-H1 | AC012-H2 |
|---|---|---|---|---|
| Lung | A549 | >10 (inhibition = 49.50% in 10 μg/ml) | 6.4 | NA |
| Liver | Huh 7 | <0.3 (inhibition = 78.92% in 0.3 μg/ml) | <0.3 (inhibition = 91.18% in 0.3 μg/ml) | NA |
| Colon rectal | RKO | >10 (inhibition = 34.67% in 10 μg/ml) | >10 (inhibition = 17.52% in 10 μg/ml) | >10 (inhibition = 31.58% in 10 μg/ml) |
|  | DLD-1 | >10 (inhibition = 20.21% in 10 μg/ml) | >10 (inhibition = 11.75% in 10 μg/ml) | >10 (inhibition = 8.31% in 10 μg/ml) |
|  | SW-480 | >10 (inhibition = 9.05% in 10 μg/ml) | >10 (inhibition = 14.78% in 10 μg/ml) | >10 (inhibition = 5.66% in 10 μg/ml) |
|  | HCT-116 | 2.29 | <0.3 (inhibition = 52.73% in 0.3 μg/ml) | >10 (inhibition = 40.27% in 10 μg/ml) |

In present invention, the bioactive compounds were purified to definite constituent and were shown to have inhibitory effects on angiogenesis at very low concentrations. Such compound not only can be purified from *Antrodia camphorata* mycelium by liquid fermentation, but also can be produced through chemical synthesis. This novel process can significantly reduce the cost of preparation and solve the issue of high demand for scarce *Antrodia camphorata*. The present invention provides a novel application of bioactive substances which are to be used as drugs through its anti-angiogenesis activity and anti-proliferative on highly proliferating cells, i.e. cancer cells. Furthermore, by modifying the substituent, the bioactive compounds display more effective properties of anti-proliferation and anticancer. According to the result of examples, AC012-H1 shows extraordinary effectiveness against colorectal cancer cell, the proliferation of which was significantly inhibited by AC012-H1, implying that the modification of substituent is successful in enhancing the efficacy against cancer cells, especially colorectal cancer cells, wherein the feature of HCT116 cell line is low expression of Bax (Wang et al. 2012), growth factor (TGFα and EGFR)-independent (Howell et al. 1998). Additionally, some compounds show excellent effectiveness against the proliferation of liver cancer cell, specifically, Huh-7, epithelial-like tumorigenic cells derived from an Asian, carrying a HFE mutation (Vecchi et al. 2009).

In summary, present invention presents an original approach for extraction of bioactive compounds and further identified their multifunctional properties in terms of anti-angiogenesis and anti-proliferation.

What is claimed is:

1. A method for treatment of cancer by administering a therapeutically effective amount of a pharmaceutical composition comprising a compound selected from the group consisting of AC006, AC007, AC009, AC011, AC012, AC007-H1, AC009-H1 and AC012-H1 or a combination of at least two of the said compounds, and
   a pharmaceutically acceptable vehicle, salt, or prodrug,
   wherein the cancer is selected from the group consisting of prostate cancer, liver cancer, melanoma, brain cancer, colorectal cancer, and lung cancer.

2. The method according to claim 1, wherein the pharmaceutical composition is administered via intravenous injection, subcutaneous injection, oral administration, or topical administration.

* * * * *